United States Patent
Masri

(10) Patent No.: US 9,022,041 B2
(45) Date of Patent: May 5, 2015

(54) TEA BASED SMOKING PRODUCT

(76) Inventor: Rodney Masri, San Diego, CA (US)

( * ) Notice: Subject to any disclaimer, the term of this patent is extended or adjusted under 35 U.S.C. 154(b) by 577 days.

(21) Appl. No.: 12/855,757

(22) Filed: Aug. 13, 2010

(65) Prior Publication Data

US 2011/0048438 A1 Mar. 3, 2011

Related U.S. Application Data

(60) Provisional application No. 61/238,263, filed on Aug. 31, 2009.

(51) Int. Cl.
| | |
|---|---|
| A24B 15/00 | (2006.01) |
| A24B 15/16 | (2006.01) |
| A24B 15/30 | (2006.01) |
| A24D 1/18 | (2006.01) |

(52) U.S. Cl.
CPC ............... *A24B 15/16* (2013.01); *A24B 15/303* (2013.01); *A24D 1/18* (2013.01)

(58) Field of Classification Search
None
See application file for complete search history.

(56) References Cited

U.S. PATENT DOCUMENTS

| | | | | |
|---|---|---|---|---|
| 2,131,160 | A * | 9/1938 | Avedikian | 131/365 |
| 2,930,719 | A | 10/1954 | Finberg | |
| 3,867,951 | A * | 2/1975 | Buchmann et al. | 131/359 |
| 4,143,666 | A * | 3/1979 | Rainer et al. | 131/359 |
| 4,694,842 | A | 9/1987 | Kobayashi | |
| 4,811,746 | A | 3/1989 | Davis | |
| 4,813,438 | A | 3/1989 | Fleming | |
| 5,513,663 | A | 5/1996 | Van Leuven | |
| 6,619,293 | B1 | 9/2003 | Siadto | |
| 6,761,176 | B2 | 7/2004 | Yoo | |
| 7,578,299 | B2 | 8/2009 | Ra | |
| 2005/0084574 | A1 * | 4/2005 | Yamada | 426/427 |
| 2007/0023060 | A1 | 2/2007 | Ra | |
| 2007/0215168 | A1 | 9/2007 | Banerjee et al. | |
| 2007/0283974 | A1 | 12/2007 | May | |
| 2008/0000488 | A1 * | 1/2008 | Nadimi et al. | 131/352 |
| 2009/0065011 | A1 | 3/2009 | Maeder et al. | |

FOREIGN PATENT DOCUMENTS

| | | |
|---|---|---|
| EP | 140670 A2 * | 5/1985 |
| EP | 0145424 | 6/1985 |

* cited by examiner

*Primary Examiner* — Richard Crispino
*Assistant Examiner* — Phu Nguyen

(57) ABSTRACT

A method of converting tea leaves into a smoking product suitable for use with a smoking device such as, but not limited to, a hookah. In one embodiment the method comprises the steps of heating a batch of sundried tea leaves in water to provide a batch of wetted tea leaves; fermenting the wetted tea leaves to provide a batch of fermented tea leaves; rinsing the fermented tea leaves with water to provide rinsed fermented tea leaves; drying the rinsed fermented tea leaves to provide dried fermented tea; and adding glycerine to the dried fermented tea leaves to provide a tea leaf based smoking product. In another embodiment a nicotine free smoking product is provided comprising of glycerin treated dried fermented tea leaves.

14 Claims, No Drawings

TEA BASED SMOKING PRODUCT

CROSS-REFERENCE TO RELATED APPLICATIONS

This application claims the benefit of priority from U.S. Provisional Patent Application Ser. No. 61/238,263, filed Aug. 31, 2009, the entire contents of which are incorporated herein by reference.

STATEMENT REGARDING FEDERALLY SPONSORED RESEARCH OR DEVELOPMENT

Not Applicable.

FIELD OF THE INVENTION

This invention relates generally to a tea based smoking composition for use in smoking apparatus such as a hookah apparatus to provide a smoking experience without the downside risks associated with smoking a tobacco product.

BACKGROUND OF THE INVENTION

As noted in U.S. Pat. No. 4,813,438 it is almost universally accepted that smoking is extremely harmful to the smoker's health and may result or contribute to physiological conditions including lung problems, increased risk of cancer and heart disease. Nicotine and tars which are a result of burning tobacco and which occur in the smoke are considered to be the major harmful ingredients. When tobacco is burned, a substantial amount of the nicotine in the tobacco product is volatilized and carried in the tobacco smoke. When the smoke is inhaled by the smoker, the volatized nicotine in the smoke is rapidly absorbed through the respiratory system and into the human circulatory system. A small amount of nicotine may also be deposited in the saliva of the smoker and on the tissues of the mouth and tongue. These deposits can cause harm to the mouth of the smoker.

It is also well documented that smoking products containing nicotine greatly increases the risk of cancers, especially lung cancer. In addition, several impairments other than lung cancer have been linked to smoking tobacco products, including pulmonary emphysema, and heart attacks. Thus, there is a continuing need for smoking products that have no nicotine or low amounts of nicotine.

U.S. Pat. No. 4,694,842 discloses a tea-containing tobacco which consists essentially of tobacco leaves, tea leaves, chrysanthemum flowers and *Cnidii rhizoma*.

U.S. Pat. No. 4,813,438 describes a tobacco substitute product and method of making same. Bran, soybean and mesquite are initially treated in a solution including sodium chloride, sweetener, glycerol and a burning aid. The soybean is toasted and formed into flakes and mixed with the bran and mesquite. This composition is treated with a flavoring and a filler may also be added.

U.S. Pat. No. 5,513,663 discloses plant parts used as a tobacco substitute in smoking compositions and in smoking substitutes. The plant parts originate from *Alchemilla vulgaris* and/or *Myrtus communis*. Mixtures containing 60-99.9% by weight of *Alchemilla vulgaris* or *Myrtus communis* are preferred. The mixture may include up to 50% by weight of one or more types of aromatic plants which are preferably selected from the group *Asperula odorata*, *Mentha piperita*, *Salvia officinalis*, *Thymus vulgaris* and *Eucalyptus globulus*, and/or extracts thereof and/or synthetic equivalent aromatic substances and/or flavorings.

U.S. Pat. No. 6,761,176 discloses a tobacco substitute composition comprised of 80-90 weight percent of *eucommia ulmoides*, 1-10 weight percent of *glycyrrhiza glabra*, and 1-10 weight percent of *periila frutescens*. A flavoring material is generally added to the composition of a tobacco such as a sodium chloride, glycerol, sweetener, spices, etc. may be added.

U.S. Pat. No. 2,930,719 describes a smoking composition one embodiment of which comprises a mixture of vegetable fibers, niacin, and rutin. The niacin and rutin each being present in amounts of at least about 0.1 percent by weight of the composition.

U.S. Pat. No. 4,811,746 describes a method of making a substitute for oral smokeless tobacco comprises the steps of applying a coating of binding agent on fragments of tea to form a cohesive material and moistening the fragments of the tea sufficiently to form a compact mass which is dissociable into portions of selectable size by hand-pinching the mass. The resulting composition resembles genuine smokeless tobacco in appearance, texture, tactile response, and mode of use. One uses the composition by taking a pinch of the composition and placing it in his mouth between the cheek and gum. The composition produces brown juices which provide an expectorate resembling that of genuine smokeless tobacco. The composition is packageable in a low profile cylindrical container of the type used to package snuff.

U.S. Pat. No. 6,619,293 describes an alternative to tobacco for both smokers and chewers is provided. A cigarette is prepared from mature tea leaves which are steamed and dried, but not withered, roasted or fermented. The tea leaves are rolled in paper and may be filtered or non-filtered. Cigarettes prepared with tea leaves processed in this manner provide acceptable taste, and may provide natural antioxidants, such as polyphenols and flavonoids, by inhalation. A chaw is made with tea leaves which have been roasted, but not fermented, and is flavored with vanilla, cinnamon or mint. Both products may be produced with natural caffeine content, or may be partially decaffeinated.

U.S. Pat. No. 7,578,299 and U.S. Publication No. 20070023060 describe a green tea-based cigarette made from a blend comprising 60-70 wt % of dry green tea leaves, each being 1-5 mm in width and 5-15 mm in length, as a main component, 25-35 wt % of cut dry tobacco leaves, and 3-7 wt % of tobacco spice; a blend comprising 80-90 wt % of the cut dry green tea leaves, 5-15 wt % of cinnamon powder and 3-7 wt % of tobacco spice; or a blend comprising 93-97 wt % of cinnamon-infused cut dry green tea leaves which are obtained by soaking 80-90 wt % of the cut dry green tea leaves in a cinnamon extract solution, and 3-7 wt % of tobacco spice. The cigarette gives flavor and tastes similar to those of conventional tobacco, catering to conventional smokers' tastes.

SUMMARY

A method of converting tea leaves into a smoking product suitable for use with a smoking device such as, but not limited to, a hookah. In one embodiment the method comprises the steps of heating a batch of sundried tea leaves in water to provide a batch of wetted tea leaves; fermenting the wetted tea leaves to provide a batch of fermented tea leaves; rinsing the fermented tea leaves with water to provide rinsed fermented tea leaves; drying the rinsed fermented tea leaves to provide dried fermented tea; and adding glycerine to the dried fermented tea leaves to provide a tea leaf based smoking product. In another embodiment, a nicotine free smoking product is provided which includes glycerin treated dried fermented tea leaves.

DETAILED DESCRIPTION OF THE INVENTION

This invention is directed to a tea based smoking composition for use in smoking apparatus such as a hookah apparatus to provide a smoking experience without the downside risks associated with smoking a tobacco product.

Tobacco based smoking products used in hookahs contain amounts of glycerine (glycerol) to moisten the tobacco product and which when smoked using a hookah generate clouds of smoke much liked by regular hookah smokers. In attempting to make a tobacco free (and hence nicotine free) smoking product for hookah smokers which generates the desired degree of smoke it is desirable that the non-tobacco smoking product absorb sufficient amounts of glycerine to produce the desired clouds of smoke. It should be understood that the invention also covers the use of propylene glycol (i.e., propane-1,2-diol) in place of glycerine.

However, getting tea leaves to absorb glycerine is very difficult. The inventor has tried many times to formulate a tea leaves based non-tobacco smoking product for use with hookah pipes but found tea leaves lacked the capacity to absorb sufficient amounts of glycerine to produce the desired cloudy smoke. Finally, after considerable effort, the inventor discovered that fermenting the tea leaves rendered them able to absorb glycerine to the desired amount. While not relying on any particular theory and certainly not intending to be limited to any particular theory, the inventor surmises that the fermentation step developed by the inventor has modified the native tea leaf to the extent necessary to render the tea leaf amenable to absorb sufficient glycerine to generate the desired hookah smoke clouds. Thus, a key objective of this invention was to overcome the difficulty of lack of absorption of glycerine by tea leaves.

A further object was to remove the tea taste associated with tea leaves to avoid making a tea leaves based hookah smoking product which generated an undesired tea flavor carried over in the hookah smoke which hookah patrons would likely find offensive or otherwise deleteriously affect the hookah smoking experience so desired by hookah smoking patrons.

The inventor has developed after many trials and setbacks a method of converting tea leaves into a smoking product suitable for use with a hookah. The steps include:

heating a batch of sundried tea leaves in water to provide a batch of wetted tea leaves;

fermenting the wetted tea leaves to provide a batch of fermented tea leaves;

rinsing the fermented tea leaves with water to provide rinsed fermented tea leaves; and drying the rinsed fermented tea leaves to provide dried fermented tea leaves to provide a tea leaf based smoking product.

In one embodiment of the invention predetermined amounts of nicotine can be added to the tea leaf based smoking product with the clear objective of aiding hooked smokers to transition from smoking tobacco based hookah products to tea leaf based smoking product with lesser predetermined amounts of nicotine until the smoker is smoking tea leaf based smoking product lacking nicotine.

Preparation of Tea Leaf Based Smoking Product

Working Example 1

[1] heat a black or green tea batch for 20-30 minutes to open up the tea leaves in 185° F. water to provide wetted tea leaves;

[2] rinse the wetted tea leaves with cold water (e.g., cold water from mains supply) to provide rinsed tea leaves;

[3] place the rinsed tea leaves in fermentation barrels for 10 days (wherein the barrels are inoculated with fermentation broth from a previous fermentation, e.g., a gallon of carryover fermentation broth from a previous fermentation);

[4] take the fermented tea leaves out of the fermentation barrels and rinse with cold water;

[5] boil the fermented tea leaves for 30 minutes, then drain water off and refill with fresh water and re-boil, repeat this step until water is clear;

[6] harvest the boiled fermented tea leaves and dry to provide dried fermented tea leaves; and

[7] working glycerine into the dried fermented tea leaves by, for example, transferring the dried fermented tea leaves to a tumbler, and while mixing add glycerine to provide a tea leaf based smoking product suitable for smoking using a hookah; this product is also referred to herein as glycerin treated dried fermented tea leaves. Corn syrup and/or flavoring can also be added along with the glycerine. (Please note: propylene glycol can be used in place of glycerine).

Preparation of Tea Leaf Based Smoking Product

Working Example 2

To a clean vessel deposit 50 lb (pounds mass) of sun dried tea leaves derived from tea plants (*Camellia sinensis*) add 25 gallons of water already heated to about 185° F. (+/−5° F.) and let tea leaves steep in the heated water for 20-30 minutes while maintaining temperature of 185° F. (+/−5° F.) with occasional stirring to avoid hot spots and to open the tea leaves. Drain water from the vessel through a screen to avoid losing tea leaves to leave a batch of wetted tea leaves inside the vessel. Rinse the wetted tea leaves by adding 25 gallons of fresh water preheated to about 185° F. (+/−5° F.) and stir gently for about 5 minutes. Drain water off through the screen and once draining is complete transfer the tea leaves to a 55 gallon fermentation barrel about ¾ full with room temperature water and containing an inoculation of fermentation broth (the fermentation broth inoculation from a previous fermentation). Add 20 lbs of corn syrup (rated at 97% purity) and fill the barrel to the brim with water at ambient room temperature. Seal the barrel and ferment for 10 days. The fermentation barrel is preferably fitted with a fermentation bung, one-way valve or functional equivalent to allow gases generated during the fermentation to escape preferably without allowing outside air into the fermentation barrel. After fermentation is completed transfer fermented tea leaves to a vessel for repeated rinses with water at ambient room temperate until water runs clear. Dry fermented tea leaves (e.g., using dry air heated to 100° F.) to provide dried fermented tea leaves. Add glycerine to the dried fermented tea leaves to provide the tea leaf based smoking product. Flavors such as food grade strawberry flavor can also be added. The amount of glycerine added should be sufficient to ensure adequate smoking properties upon smoking the tea leaf based smoking product using a hookah (40-60% by weight of glycerine in the final product is adequate). (Please note: propylene glycol can be used in place of glycerine). The term "by weight" means relative to the total weight of the final product; thus, "40-60% by weight of glycerine means 40-60% by weight of the total weight of the final product. The terms "final product" and "blend" are regarded as equivalent terms.

Preparation of Tea Leaf Based Smoking Product

Working Example 3

To a clean vessel deposit 50 lb (pounds mass) of sun dried tea leaves derived from green tea plants (e.g., conventional sencha) add 25 gallons of water already heated to about 185° F. (+/−5° F.) and let tea leaves steep in the heated water for 20-30 minutes while maintaining temperature of 185° F. (+/−5° F.) with occasional stirring to avoid hot spots and to open the tea leaves. Drain water from the vessel through a screen to avoid losing tea leaves to leave a batch of wetted tea leaves inside the vessel. Rinse the wetted tea leaves by adding 25 gallons of fresh water preheated to about 185° F. (+/−5° F.) and stir gently for about 5 minutes. Drain water off through the screen and once draining is complete transfer the tea leaves to a 55 gallon fermentation barrel about ¾ full with room temperature water and containing an inoculation of fermentation broth (the fermentation broth inoculation from a previous fermentation). Add 20 lbs of corn syrup (rated at 97% purity) and fill the barrel to the brim with water at ambient room temperature. Seal the barrel and ferment for 10 days. The fermentation barrel is preferably fitted with a fermentation bung, one-way valve or functional equivalent to allow gases generated during the fermentation to escape preferably without allowing outside air into the fermentation barrel. After fermentation is completed transfer fermented tea leaves to a vessel for repeated rinses with water at ambient room temperate until water runs clear. Dry fermented tea leaves (e.g., using dry air heated to 100° F.) to provide dried fermented tea leaves. Add glycerine to the dried fermented tea leaves to provide the tea leaf based smoking product. Flavors such as food grade strawberry flavor can also be added. Also, a sweetener can be added such as honey. The amount of glycerine added should be sufficient to ensure adequate smoking properties upon smoking the tea leaf based smoking product using a hookah. (Please note: propylene glycol can be used in place of glycerine.)

In one embodiment, blends according to the invention comprise: tea leaves 15 to 25% by weight (i.e., 15-25% by weight), glycerin (or propylene glycol) at 40-60% by weight, sweetener at 10-25% by weight, and flavoring at 1 to 5% by weight. Any suitable flavoring may be used. For example, suitable flavorings included those selected from the list consisting of: blueberry, double apple, fruit punch, strawberry, grape, green apple, guava, orange, melon, margarita, mango, lemonade, kiwi, watermelon, spearmint, pumpkin pie, pineapple, pinacolada, peanut butter, and peach, alone or in combination. Suitable sweeteners include those selected from the list consisting of: honey, molasses, corn syrup, alone or in combination.

In one embodiment of the present invention is a blend comprising of: glycerine 45-65% by weight, and tea leaves 35-55% by weight. In one embodiment of the present invention is a blend comprising of: propylene glycol 45-65% by weight, and tea leaves 35-55% by weight.

What is claimed:

1. A method of converting tea leaves into a smoking product, comprising the steps:

heating a batch of sundried tea leaves in water to provide a batch of wetted tea leaves;
rinsing the wetted tea leaves to provide rinsed tea leaves;
placing the rinsed tea leaves in a vessel;
inoculating the rinsed tea leaves with fermentation broth;
fermenting the rinsed tea leaves to provide a batch of fermented tea leaves;
rinsing the fermented tea leaves with water to provide rinsed fermented tea leaves;
drying the rinsed fermented tea leaves to provide dried fermented tea; and
working glycerine into the dried fermented tea leaves to provide a tea leaf based smoking product.

2. The method according to claim 1, wherein propylene glycol is used in place of glycerine.

3. The method according to claim 1, wherein the sundried tea leaves are sundried *Camellia sinensis*.

4. The method according to claim 1, wherein the sundried tea leaves are sundried conventional sencha.

5. The method according to claim 1, wherein the tea leaf based smoking product is smoked using a smoking device.

6. The method according to claim 1, wherein the tea leaf based smoking product is smoked using a hookah.

7. The method according to claim 1, wherein corn syrup is added along with the glycerine to provide the tea leaf based smoking product.

8. The method according to claim 1, wherein the fermentation time is 10 days.

9. The method according to claim 1, wherein the vessel is a barrel.

10. The method according to claim 9 further comprising the step of sealing the barrel from outside air.

11. The method according to claim 10 further comprising the step of allowing fermentation gases to escape from the barrel without allowing outside air into the barrel.

12. The method according to claim 1, wherein the step of inoculating the rinsed tea leaves with fermentation broth is performed by inoculating the rinsed tea leaves with fermentation broth from a previous fermentation.

13. A method of converting tea leaves into a smoking product, comprising the steps:

heating a batch of sundried tea leaves in water to provide a batch of wetted tea leaves;
rinsing the wetted tea leaves to provide rinsed tea leaves;
placing the rinsed tea leaves, an inoculation of fermentation broth, and corn syrup in a vessel;
fermenting the rinsed tea leaves to provide a batch of fermented tea leaves;
rinsing the fermented tea leaves with water to provide rinsed fermented tea leaves;
drying the rinsed fermented tea leaves to provide dried fermented tea; and
working glycerine into the dried fermented tea leaves to provide a tea leaf based smoking product.

14. The method according to claim 13, wherein the vessel is sealed from outside air after the step of placing the rinsed tea leaves, the inoculation of fermentation broth, and corn syrup in the vessel.

* * * * *